United States Patent
Kurimoto et al.

(10) Patent No.: US 6,403,572 B1
(45) Date of Patent: Jun. 11, 2002

(54) PRODUCING Z-ISOMER OF HYDROGEN BROMIDE SALT OF 2-AMINOTHIAZOLE DERIVATIVE

(75) Inventors: Isao Kurimoto; Norihiko Hirata, both of Suita; Akihiko Nakamura; Yuichiro Aratake, both of Takatsuki, all of (JP)

(73) Assignees: Sumitomo Chemical Co., Ltd.; Shionogi & co., Ltd., both of Osaka (JP)

( * ) Notice: Subject to any disclaimer, the term of this patent is extended or adjusted under 35 U.S.C. 154(b) by 0 days.

(21) Appl. No.: 09/991,728

(22) Filed: Nov. 26, 2001

Related U.S. Application Data

(62) Division of application No. 09/437,599, filed on Nov. 10, 1999, now Pat. No. 6,340,763.

(30) Foreign Application Priority Data

| Feb. 4, 1998 | (JP) | ............................................ 11-027198 |
| Nov. 12, 1998 | (JP) | ............................................ 10-322050 |
| Jun. 29, 1999 | (JP) | ............................................ 11-183671 |

(51) Int. Cl.$^7$ ............................................ C07D 277/40
(52) U.S. Cl. ...................................................... 514/194
(58) Field of Search ........................................ 548/144

(56) References Cited

U.S. PATENT DOCUMENTS 4,782,162 A    11/1988    Boberg et al.

FOREIGN PATENT DOCUMENTS

| EP | 0049448 A2 | 4/1982 |
| EP | 0337643 A2 | 10/1989 |
| EP | 0421752 A2 | 4/1991 |
| EP | 0467647 A2 | 1/1992 |

OTHER PUBLICATIONS

Wilberg, Laboratory Technique in Organic Chemistry, pp. 99–104, 1960.

*Primary Examiner*—Robert Gerstl

(74) *Attorney, Agent, or Firm*—Birch, Stewart, Kolasch & Birch, LLP

(57) ABSTRACT

There is disclosed a process for producing an acid salt of a (Z)-2-aminothiazole compound of the formula (I):

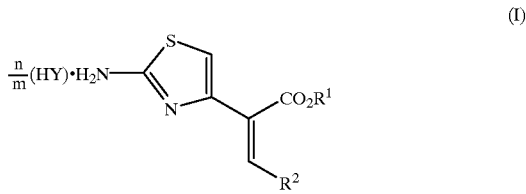

(I)

wherein $R^1$ and $R^2$ independently represent an alkyl group having 1 to 5 carbon atoms, Y represents a halogen atom, $-OSO_3H$ or $-OPO(OH)_2$, m indicates the valence number of an inorganic acid of the formula: HY wherein Y represents the same as defined above, and n indicates an integer of 1 or 2, which process is characterized by:

reacting an acid salt of a 2-aminothiazole compound of the formula (II):

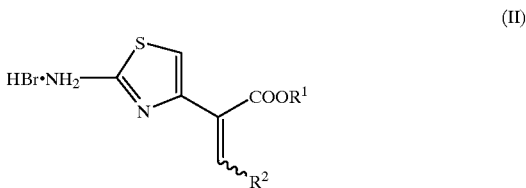

(II)

wherein $R^1$ and $R^2$ independently represent an alkyl group having 1 to 5 carbon atoms, X represents a bromine atom or an iodine atom, and the wavy line means that this compound is a mixture of the E- and Z-isomers, with the inorganic acid of the formula HY.

5 Claims, No Drawings

PRODUCING Z-ISOMER OF HYDROGEN BROMIDE SALT OF 2-AMINOTHIAZOLE DERIVATIVE

This application is a divisional of co-pending application Ser. No. 09/437,599, filed on Nov. 10, 1999, U.S. Pat. No. 6,370,783 the entire contents of which are hereby incorporated by reference and for which priority is claimed under 35 U.S.C. §120; and this application claims priority of Application No. 10-322050, 11-027198, and 11-183671 filed in Japan on Nov. 12, 1998; Feb. 4, 1999; and Jun. 29, 1999, respectively, under 35 U.S.C. §119.

FIELD OF THE INVENTION

The present invention relates to a process for producing a hydrogen bromide salt of a (Z)-2-aminothiazole derivative which is useful as an intermediate of pharmaceuticals, for example, an intermediate for constructing a side chain part of the antibiotics disclosed in EP467647B1, which corresponds to Japanese Patent No. 2618119.

DESCRIPTION OF THE RELATED ART

A process for producing a hydrogen bromide salt of the (Z)-2-aminothiazole derivative is disclosed in Preparation 6 of EP467647B1, however, the process is not always satisfactory as an industrial production method in that no reproducible particulars on how to control the exothermic reaction is disclosed. Hence an improved process has been desired.

SUMMARY OF THE INVENTION

An object of the invention is to provide a method for producing an acid salt of a (Z)-2-aminothiazole derivative of the formula I as depicted below.

Another object of the invention is to provide an industrially advantageous reaction method, particularly a continuous method, for preferentially producing a Z-isomer of a hydrogen bromide salt of a 2-aminothiazole derivative of the formula (I), while effectively controlling the exothermic reaction on an industrial scale production.

The present invention provides:

1. a process for producing an acid salt of a (Z)-2-aminothiazole compound of the formula (I):

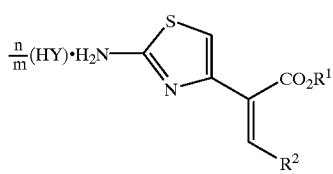

(I)

wherein
   $R^1$ and $R^2$ independently represent an alkyl group having 1 to 5 carbon atoms,
   Y represents a halogen atom, $-OSO_3H$ or $-OPO(OH)_2$,
   m indicates the valence number of an inorganic acid of HY and
   n indicates an integer of 1 or 2,
which process comprises:
   reacting an acid salt of a 2-aminothiazole compound of the formula (II):

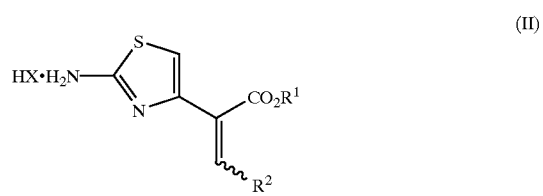

(II)

wherein $R^1$ and $R^2$ independently represent an alkyl group having 1 to 5 carbon atoms, the wavy line means that this compound is a mixture of the E- and Z-isomers, and X represents a bromine atom or an iodine atom, with an inorganic acid of the formula (III):

HY (III)

wherein Y represents a halogen atom, $-OSO_3H$ or $-OPO(OH)_2$;

2. a continuous process for preferentially producing a Z-isomer of a hydrogen bromide salt of a 2-aminothiazole derivative of the formula (IV):

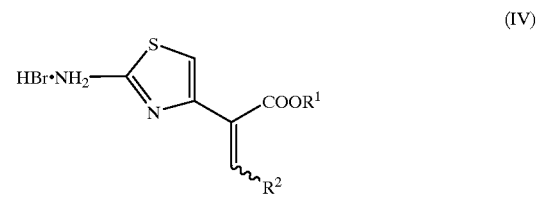

(IV)

wherein $R^1$ and $R^2$ independently represent a lower alkyl group having 1 to 5 carbon atoms, and the wavy line means that this compound is a mixture of the E- and Z-isomers,
which process comprises:
   continuously feeding thiourea and a 2-alkylidene-4-bromoacetoacetic acid ester of the formula (V):

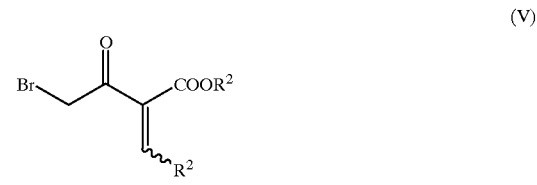

(V)

wherein $R^1$ and $R^2$ have the same meaning as defined above, and the wavy line means that this compound is a mixture of the E- and Z-isomers, into a reaction vessel having at least one agitator,
   reacting the thiourea and the compound of the formula (V) together in the reaction vessel for a sufficient residence time for the conversion of the compound of the formula (V) to the compound of the formula (IV), and
   withdrawing a resulting reaction mixture containing the compound of the formula (IV) from the reaction vessel as an effluent; and 3. a process for preferentially producing a Z-isomer of a hydrogen bromide salt of a 2-aminothiazole derivative of the formula (IV) as defined above,
which process comprises:
   reacting thiourea and a 2-alkylidene-4-bromoacetoacetic ester of the formula (V) as defined above, wherein the reaction temperature of the reaction is maintained at a temperature of −10 to +45° C. and the reaction time Rt of the reaction is defined by the following inequality:

$$60e^{(-0.15T)} \leq Rt \leq 180e^{(-0.1T)},$$

wherein "T" means a reaction temperature.

In the present invention the term "Rt" stands for both "Reaction Time" (when reference a batch reaction in a reaction vessel), and "Residence Time" (when reference continuous reaction in a reaction vessel).

DESCRIPTION OF THE PREFERRED EMBODIMENTS

First, a description will be made to the first aspect of the present invention drawn to the process for producing an acid salt of a (Z)-2-aminothiazole compound of the formula (I), which process comprises reacting an acid salt of a 2-aminothiazole compound of the formula (II) with an inorganic acid of the formula (III).

Examples of the lower alkyl group having 1 to 5 carbon atoms for $R^1$ and $R^2$ of the formulae (I), (II) and (VI) each independently include a methyl group, an ethyl group, an n-propyl group, an isopropyl group, an n-butyl group, an isobutyl group, a sec-butyl group, a t-butyl group, a n-pentyl group and a neopentyl group.

Examples of the lower alkyl group having 1 to 5 carbon atoms for $R^1$ and $R^2$ of the formulae (IV) and (V) described for the second aspect of the present invention also include the same as described above.

The group Y in the acid salt of the (Z)-2-aminothiazole compound of the formulae (I) and (III) represents a halogen atom such as chlorine, bromine and the like, or represents —OSO$_3$H or —OPO(OH)$_2$.

The X in the acid salt of the 2-aminothiazole compound of the formula (II) represents a bromine atom or an iodine atom.

Examples of the acid salt of the 2-aminothiazole compound of the formula (II) include hydrogen bromide salts or hydrogen iodide salts of the following compounds:

methyl 2-(2-aminothiazole-4-yl)-2-butenoate,
ethyl 2-(2-aminothiazole-4-yl)-2-butenoate,
n-propyl 2-(2-aminothiazole-4-yl)-2-butenoate,
isopropyl 2-(2-aminothiazole-4-yl)-2-butenoate,
n-butyl 2-(2-aminothiazole-4-yl)-2-butenoate,
t-butyl 2-(2-aminothiazole-4-yl)-2-butenoate,
n-pentyl 2-(2-aminothiazole-4-yl)-2-butenoate,
methyl 2-(2-aminothiazole-4-yl)-2-pentenoate,
ethyl 2-(2-aminothiazole-4-yl)-2-pentenoate,
n-propyl 2-(2-aminothiazole-4-yl)-2-pentenoate,
isopropyl 2-(2-aminothiazole-4-yl)-2-pentenoate,
n-butyl 2-(2-aminothiazole-4-yl)-2-pentenoate,
t-butyl 2-(2-aminothiazole-4-yl)-2-pentenoate,
n-pentyl 2-(2-aminothiazole-4-yl)-2-pentenoate,
methyl 2-(2-aminothiazole-4-yl)-2-hexenoate,
ethyl 2-(2-aminothiazole-4-yl)-2-hexenoate,
n-propyl 2-(2-aminothiazole-4-yl)-2-hexenoate,
isopropyl 2-(2-aminothiazole-4-yl)-2-hexenoate,
n-butyl 2-(2-aminothiazole-4-yl)-2-hexenoate,
t-butyl 2-(2-aminothiazole-4-yl)-2-hexenoate,
n-pentyl 2-(2-aminothiazole-4-yl)-2-hexenoate,
methyl 2-(2-aminothiazole-4-yl)-4-methyl-2-pentenoate,
ethyl 2-(2-aminothiazole-4-yl)-4-methyl-2-pentenoate,
n-propyl 2-(2-aminothiazole-4-yl)-4-methyl-2-pentenoate,
isopropyl 2-(2-aminothiazole-4-yl)-4-methyl-2-pentenoate,
n-butyl 2-(2-aminothiazole-4-yl)-4-methyl-2-pentenoate,
t-butyl 2-(2-aminothiazole-4-yl)-4-methyl-2-pentenoate,
n-pentyl 2-(2-aminothiazole-4-yl)-4-methyl-2-pentenoate,
methyl 2-(2-aminothiazole-4-yl)-2-heptenoate,
ethyl 2-(2-aminothiazole-4-yl)-2-heptenoate,
n-propyl 2-(2-aminothiazole-4-yl)-2-heptenoate,
isopropyl 2-(2-aminothiazole-4-yl)-2-heptenoate,
n-butyl 2-(2-aminothiazole-4-yl)-2-heptenoate,
t-butyl 2-(2-aminothiazole-4-yl)-2-heptenoate,
n-pentyl 2-(2-aminothiazole-4-yl)-2-heptenoate,
methyl 2-(2-aminothiazole-4-yl)-4,4-dimethyl-2-pentenoate,
ethyl 2-(2-aminothiazole-4-yl)-4,4-dimethyl-2-pentenoate,
n-propyl 2-(2-aminothiazole-4-yl)-4,4-dimethyl-2-pentenoate,
isopropyl 2-(2-aminothiazole-4-yl)-4,4-dimethyl-2-pentenoate,
n-butyl 2-(2-aminothiazole-4-yl)-4,4-dimethyl-2-pentenoate,
t-butyl 2-(2-aminothiazole-4-yl)-4,4-dimethyl-2-pentenoate,
n-pentyl 2-(2-aminothiazole-4-yl)-4,4-dimethyl-2-pentenoate,
methyl 2-(2-aminothiazole-4-yl)-2-octenoate,
ethyl 2-(2-aminothiazole-4-yl)-2-octenoate,
n-propyl 2-(2-aminothiazole-4-yl)-2-octenoate,
isopropyl 2-(2-aminothiazole-4-yl)-2-octenoate,
n-butyl 2-(2-aminothiazole-4-yl)-2-octenoate,
t-butyl 2-(2-aminothiazole-4-yl)-2-octenoate and
n-pentyl 2-(2-aminothiazole-4-yl)-2-octenoate, and mixtures of two or more of these acid salts.

Z-isomer rich hydrogen bromide salts of the above-described 2-aminothiazole derivative are preferably used in the present process and can be obtained by a known method or by the methods of the present invention described below.

Examples of the inorganic acid of the formula (III) include hydrogen halide such as hydrogen chloride and hydrogen bromide, sulfuric acid, phosphoric acid, and the like. Preferred are hydrogen chloride and hydrogen bromide, and hydrogen chloride is used more preferably. Although the inorganic acid is usually used singly, mixtures of two or more inorganic acids can be used. The amount of the inorganic acid to be used is 0.3 to 10 moles, preferably 0.5 to 5 moles per mole of the acid salt of the 2-aminothiazole compound (II).

Although an anhydrous inorganic acid such as a gaseous inorganic acid can be used, an aqueous solution of the inorganic acid is usually used. The concentration of the aqueous acid solution is usually 2 to 99%, preferably 4 to 70%.

Alternatively, a solution of the anhydrous inorganic acid (III) absorbed in an organic solvent also can be employed. Examples of the organic solvent include:

aromatic hydrocarbons such as benzene, toluene and xylene;
aliphatic hydrocarbons such as hexane and heptane;
halogenated hydrocarbons such as dichloromethane, 1,2-dichloroethane, chloroform, 1-chlorobutane and chlorobenzene,
ethers such as diethyl ether, t-butyl methyl ether, tetrahydrofuran, 1,2-dimethoxyethane, diglyme and triglyme;
ketones such as acetone, methyl ethyl ketone and methyl isobutyl ketone;
amides such as N,N-dimethylformamide, N,N-dimethylacetamide, N-methylpyrrolidone and 1,3-dimethyl-2-imidazolidinone;
alcohols such as methanol, ethanol, 1-propanol, 2-propanol and 1-butanol; and nitriles such as acetonitrile. Such organic solvents may be used either singly or in mixtures of two or more of them.

The amount of the organic solvent to be used is usually 0.2 to 50 parts, preferably 0.5 to 20 parts per 1 part by weight of the inorganic acid (III).

The reaction between the acid salt of the 2-aminothiazole compound of the formula (II) and the inorganic acid of the formula (III) is usually carried out in the presence of a solvent. Examples of the solvent include those as exemplified above for absorbing gaseous inorganic acid as well as water.

Such solvents are used singly or in combinations of two or more of them. Preferably, a water miscible organic solvent is used.

Examples of such a water miscible organic solvent include:
ethers such as 1,2-dimethoxyethane, diglyme and triglyme;
ketones such as acetone and methyl ethyl ketone;
amides such as N,N-dimethylformamide, N,N-dimethylacetamide, N-methylpyrrolidone and 1,3-dimethyl-2-imidazolidinone;
alcohols such as methanol, ethanol and 2-propanol;
nitriles such as acetonitrile.

The amount of the organic solvent or water to be used is usually 0.5 to 100 parts, preferably 1 to 50 parts per 1 part by weight of the acid salt of the 2-aminothiazole compound (II).

The reaction of the acid salt of the 2-aminothiazole compound (II) with the inorganic acid (III) is carried out, for example, by adding an aqueous solution of the inorganic acid (III) to a solution containing the acid salt of the 2-aminothiazole compound (II). Alternatively, the solution containing the acid salt of the 2-aminothiazole compound (II) may be added to the aqueous solution of the inorganic acid (III).

The reaction is carried out at temperatures not less than the solidifying point of the reaction mixture. The reaction temperature is usually −40 to 40° C., preferably −20 to 20° C.

The reaction time is not particularly limited, and usually is about 0.5 to 48 hours.

The acid salt of the (Z)-2-aminothiazole compound of the formula (I) obtained may be added as a seed crystal before or during mixing the acid salt of the 2-aminothiazole compound (II) and the inorganic acid (III), if necessary. Such an addition of the seed crystal may result in smooth precipitation of crystals from the reaction mixture.

After completion of the reaction, the acid salt of the (Z)-2-aminothiazole compound of the formula (I) can be isolated as crystals by filtering the precipitates from the reaction mixture.

The crystals of the acid salt of the (Z)-2-aminothiazole compound (I) thus obtained may be washed with a solvent, if necessary. Examples of the solvent that can be used for washing the crystals include those described above for the reaction of the acid salt of the 2-aminothiazole compound (II) with the inorganic acid (III). Such solvents are used singly or in combination of two or more of them.

The amount of the solvent used is usually 0.1 to 20 parts, preferably 0.3 to 10 parts by 1 part by weight of the acid salt (II) of the 2-aminothiazole compound.

The crystals are washed usually at −40 to 40° C., preferably −20 to 20° C.

Thus obtained crystals of the acid salt of the (Z)-2-aminothiazole compound of the formula (I) can be dried in a conventional manner. Alternatively, crystals containing the organic solvents used in the reaction and/or washing can be used with no problem without being dried.

When a solvent containing water is used as a solvent in the reaction and/or washing, the acid salt of the (Z)-2-aminothiazole compound of the formula (I) obtained may contain crystal water. Even in such a case, the acid salt of the (Z)-2-aminothiazole compound (I) can be produced and used with no problem.

Thus the acid salt of the (Z)-2-aminothiazole compound of the formula (I) can be obtained. Examples of the acid salt of the (Z)-2-aminothiazole compound (I) include: hydrochlorides, hydrobromides, hydriodides, dihydrochlorides, dihydrobromides, dihydriodides, hydrogen sulfates and 1/3-phosphates of the following compounds:

methyl (Z)-2-(2-aminothiazole-4-yl)-2-butenoate,
ethyl (Z)-2-(2-aminothiazole-4-yl)-2-butenoate,
n-propyl (Z)-2-(2-aminothiazole-4-yl)-2-butenoate,
isopropyl (Z)-2-(2-aminothiazole-4-yl)-2-butenoate,
n-butyl (Z)-2-(2-aminothiazole-4-yl)-2-butenoate,
t-butyl (Z)-2-(2-aminothiazole-4-yl)-2-butenoate,
n-pentyl (Z)-2-(2-aminothiazole-4-yl)-2-butenoate,
methyl (Z)-2-(2-aminothiazole-4-yl)-2-pentenoate,
ethyl (Z)-2-(2-aminothiazole-4-yl)-2-pentenoate,
n-propyl (Z)-2-(2-aminothiazole-4-yl)-2-pentenoate,
isopropyl (Z)-2-(2-aminothiazole-4-yl)-2-pentenoate,
n-butyl (Z)-2-(2-aminothiazole-4-yl)-2-pentenoate,
t-butyl (Z)-2-(2-aminothiazole-4-yl)-2-pentenoate,
n-pentyl (Z)-2-(2-aminothiazole-4-yl)-2-pentenoate,
methyl (Z)-2-(2-aminothiazole-4-yl)-2-hexenoate,
ethyl (Z)-2-(2-aminothiazole-4-yl)-2-hexenoate,
n-propyl (Z)-2-(2-aminothiazole-4-yl)-2-hexenoate,
isopropyl (Z)-2-(2-aminothiazole-4-yl)-2-hexenoate,
n-butyl (Z)-2-(2-aminothiazole-4-yl)-2-hexenoate,
t-butyl (Z)-2-(2-aminothiazole-4-yl)-2-hexenoate,
n-pentyl (Z)-2-(2-aminothiazole-4-yl)-2-hexenoate,
methyl (Z)-2-(2-aminothiazole-4-yl)-4-methyl-2-pentenoate,
ethyl (Z)-2-(2-aminothiazole-4-yl)-4-methyl-2-pentenoate,
n-propyl (Z)-2-(2-aminothiazole-4-yl)-4-methyl-2-pentenoate,
isopropyl (Z)-2-(2-aminothiazole-4-yl)-4-methyl-2-pentenoate,
n-butyl (Z)-2-(2-aminothiazole-4-yl)-4-methyl-2-pentenoate,
t-butyl (Z)-2-(2-aminothiazole-4-yl)-4-methyl-2-pentenoate,
n-pentyl (Z)-2-(2-aminothiazole-4-yl)-4-methyl-2-pentenoate,
methyl (Z)-2-(2-aminothiazole-4-yl)-2-heptenoate,
ethyl (Z)-2-(2-aminothiazole-4-yl)-2-heptenoate,
n-propyl (Z)-2-(2-aminothiazole-4-yl)-2-heptenoate,
isopropyl (Z)-2-(2-aminothiazole-4-yl)-2-heptenoate,
n-butyl (Z)-2-(2-aminothiazole-4-yl)-2-heptenoate,
t-butyl (Z)-2-(2-aminothiazole-4-yl)-2-heptenoate,
n-pentyl (Z)-2-(2-aminothiazole-4-yl)-2-heptenoate,
methyl (Z)-2-(2-aminothiazole-4-yl)-4,4-dimethyl-2-pentenoate,
ethyl (Z)-2-(2-aminothiazole-4-yl)-4,4-dimethyl-2-pentenoate,
n-propyl (Z)-2-(2-aminothiazole-4-yl)-4,4-dimethyl-2-pentenoate,
isopropyl (Z)-2-(2-aminothiazole-4-yl-4,4-dimethyl-2-pentenoate,
n-butyl (Z)-2-(2-aminothiazole-4-yl)-4,4-dimethyl-2-pentenoate,
t-butyl (Z)-2-(2-aminothiazole-4-yl)-4,4-dimethyl-2-pentenoate,
n-pentyl (Z)-2-(2-aminothiazole-4-yl) -4,4-dimethyl-2-pentenoate,
methyl (Z)-2-(2-aminothiazole -4-yl)-2-octenoate, ethyl (Z)-2-(2-aminothiazole-4-yl)-2-octenoate,
n-propyl (Z)-2-(2-aminothiazole-4-yl)-2-octenoate,
isopropyl (Z)-2-(2-aminothiazole-4-yl)-2-octenoate,
n-butyl (Z)-2-(2-aminothiazole-4-yl)-2-octenoate,
t-butyl (Z)-2-(2-aminothiazole-4-yl)-2-octenoate and
n-pentyl (Z)-2-(2-aminothiazole-4-yl)-2-octenoate.

When the substituent X in the acid salt of the 2-aminothiazole compound of the formula (II) is not the same as the group Y in the inorganic acid of the formula (III), the acid salt of a (Z)-2-aminothiazole compound of the formula (I) may be obtained as a mixed acid salt of the (Z)-2-aminothiazole compound of the formula (I) as described above.

The acid salt of the (Z)-2-aminothiazole compound of the formula (I) can, for example, be converted to a free (Z)-2-aminothiazole compound by allowing it to react with a base such as sodium hydrogencarbonate, if necessary.

The acid salt of the (Z)-2-aminothiazole compound (I) as described above can be manufactured and used with encountering no problem.

The acid salt of the 2-aminothiazole compound of the formula (II) that is used in the above-described process, can be prepared, for example, by reacting a halogenated compound of the formula (V):

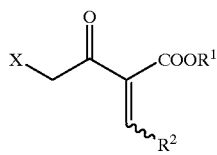

(VI)

wherein
$R^1$ and $R^2$ independently represent an alkyl group having 1 to 5 carbon atoms,
X represents a bromine atom or an iodine atom and the wavy line means that this compound is a mixture of the E- and Z-isomers, with thiourea under similar conditions as described below, but manufacturing conditions or methods of the salt are not particularly limited thereto.

Next, a description will be made to the second aspect of the present invention regarding the continuous process for preferentially producing the compound of the formula (IV) from a 2-alkylidene-4-bromoacetoacetic acid ester of the formula (V).

Although the 2-alkylidene-4-bromoacetoacetic ester of the formula (VI) to be used in the second aspect of the present invention can be obtained, for example, according to the method disclosed in the EP 0467647B1, the production method of the compound is not restricted to the disclosed process.

Specific examples of the 2-alkylidene-4-bromoacetoacetic ester of the formula (VI) include:

methyl 2-ethylidene-4-bromoacetoacetate,
ethyl 2-ethylidene-4-bromoacetoacetate,
n-propyl 2-ethylidene-4-bromoacetoacetate,
i-propyl 2-ethylidene-4-bromoacetoacetate,
n-butyl 2-ethylidene-4-bromoacetoacetate,
t-butyl 2-ethylidene-4-bromoacetoacetate,
n-pentyl 2-ethylidene-4-bromoacetoacetate,
methyl 2-propylidene-4-bromoacetoacetate,
ethyl 2-propylidene-4-bromoacetoacetate,
n-propyl 2-propylidene-4-bromoacetoacetate,
i-propyl 2-propylidene-4-bromoacetoacetate,
n-butyl 2-propylidene-4-bromoacetoacetate,
t-butyl 2-propylidene-4-bromoacetoacetate,
n-pentyl 2-propylidene-4-bromoacetoacetate,
methyl 2-butylidene-4-bromoacetoacetate,
ethyl 2-butylidene-4-bromoacetoacetate,
n-propyl 2-butylidene-4-bromoacetoacetate,
i-propyl 2-butylidene-4-bromoacetoacetate,
n-butyl 2-butylidene-4-bromoacetoacetate,
t-butyl 2-butylidene-4-bromoacetoacetate,
n-pentyl 2-butylidene-4-bromoacetoacetate,
methyl 2-(2-methylpropylidene)-4-bromoacetoacetate,
ethyl 2-(2-methylpropylidene)-4-bromoacetoacetate,
n-propyl 2-(2-methylpropylidene)-4-bromoacetoacetate,
i-propyl 2-(2-methylpropylidene)-4-bromoacetoacetate,
n-butyl 2-(2-methylpropylidene)-4-bromoacetoacetate,
t-butyl 2-(2-methylpropylidene)-4-bromoacetoacetate,
n-pentyl 2-(2-methylpropylidene)-4-bromoacetoacetate,
methyl 2-pentylidene-4-bromoacetoacetate,
ethyl 2-pentylidene-4-bromoacetoacetate,
n-propyl 2-pentylidene-4-bromoacetoacetate,
i-propyl 2-pentylidene-4-bromoacetoacetate,
n-butyl 2-pentylidene-4-bromoacetoacetate,
t-butyl 2-pentylidene-4-bromoacetoacetate,
n-pentyl 2-pentylidene-4-bromoacetoacetate,
methyl 2-(2,2-dimethylpropylidene)-4-bromoacetoacetate,
ethyl 2-(2,2-dimethylpropylidene)-4-bromoacetoacetate,
n-propyl 2-(2,2-dimethylpropylidene)-4-bromoacetoacetate,
i-propyl 2-(2,2-dimethylpropylidene)-4-bromoacetoacetate,
n-butyl 2-(2,2-dimethylpropylidene)-4-bromoacetoacetate,
t-butyl 2-(2,2-dimethylpropylidene)-4-bromoacetoacetate,
n-pentyl 2-(2,2-dimethylpropylidene)-4-bromoacetoacetate,
methyl 2-hexylidene-4-bromoacetoacetate,
ethyl 2-hexylidene-4-bromoacetoacetate,
n-propyl 2-hexylidene-4-bromoacetoacetate,
i-propyl 2-hexylidene-4-bromoacetoacetate,
n-butyl 2-hexylidene-4-bromoacetoacetate,
t-butyl 2-hexylidene-4-bromoacetoacetate,
n-pentyl 2-hexylidene-4-bromoacetoacetate, and the like.

The amount of thiourea to be used is usually from 0.5 to 10 moles, preferably from 0.9 to 5 moles per mol of the 2-alkylidene-4-bromoacetoacetic ester of the formula (VI).

In the continuous process of the present invention, the reaction is preferably conducted so that the resulting mixture is preferably maintained at a predetermined temperature (e.g., −10 to +45° C.) so that undesirable side reactions are reduced, and the reactor is designed to have sufficient residence time for the conversion of the fed reactants.

The solution of the 2-alkylidene-4-bromoacetoacetic acid ester and a solution of thiourea are usually continuously charged by a pump such as a gear pump, syringe pump and the like into the reaction vessel.

The reaction vessel usually contains a transfer line connected ahead to a tubular reactor which may be further connected with a transfer tubular line. The solutions of the reactants (thiourea and the compound of the formula (V)) are usually continuously fed into the transfer line connected ahead to a tubular reactor or directly into the reactor in which the reactants are thoroughly mixed by an agitator equipped thereto, and further conversion of the reactants is allowed in the following transfer tubular line, if necessary.

Examples of the reaction vessel to be used in the present invention include a tubular reactor having at least one agitator arranged singly or in series which can cause a sufficient turbulent flow to the charged reactant solutions.

Examples of the agitator include:
a static mixer, wherein variously shaped vanes causing a turbulent flow of the reactant solutions are placed in a tubular casing, an agitator wherein a vane placed in a tubular casing is rotated so as to make a turbulent flow as described above, an agitator having a vane fixed to the inner wall of a tubular casing and a stirrer fixed to a shaft that is mounted in the tubular casing and reciprocates in the axis direction, and an agitator having a helical vane fixed to a shaft which is set in the tubular casing and the shaft is connected to a vibration source, wherein the helical vane and the tubular casing form a helical passage for the reactant solution.

Among these, preferably employed are:

a static mixer (e.g., Noritake Static Mixer manufactured by Noritake Company, Limited, TK-ROSS LPD Mixer and Motionless Mixer manufactured by Tokusyukika-kogyou, Ltd, Sulzer Mixer manufacture by Sumitomo Heavy Industries, Ltd, Myu Mixer manufactured by Iken Kogyou, Ltd, Square Mixer manufacture by Sakura Seisakusyo, Ltd, Satake Multiline Mixer manufactured by Satake Kagaku Kikai Kogyou, Ltd and Pipeline Agitator manufacture by Shimazaki Seisakusyo, Ltd.), an agitator having a helical vane fixed to a shaft which is set in the tubular casing and the shaft is connected to a vibration source or to a crankshaft of a motor, thereby forming a helical passage for the reactant solutions as disclosed in JP 4-235729 A and Journal of Fermentation and Bioengineering Vol. 78, No.4.pp293–297, 1994, the whole disclosures of which are incorporated herein by reference.

The tubular reactor of the present invention may be further partitioned with a plurality of perforated partition plates which are set in the tubular line to mix the reactant solution flow in a plurality of stages.

A mixed reaction solution obtained by feeding and mixing a solution of the 2-alkylidene-4-bromoacetoacetic ester and a solution of thiourea in a tubular reactor may thereafter be passed through an ordinary tubular line, i.e., pipe to be retained for a desired residence time (reaction time).

The reactants of the formula (V) and thiouera are usually fed into the reactor as a solution in a solvent. Examples of the solvent to be used include those organic solvents used in the first aspect of the present invention. The solvents may be used singly or in combination of two or more of them. The amount of the solvent used is not particularly limited and is usually from 0.5 to 100 parts, preferably from 1 to 30 parts per 1 part by weight of the 2-alkylidene-4-bromoacetoacetic ester of the formula (V).

The amount of the solvent to be used for dissolving thiourea is such an amount that does not allow to precipitate the thiourea at a reaction temperature described below. Preferably used are amide solvent as described above to dissolve the thiourea.

The reaction is preferably conducted at a temperature of from −10 to 45° C. so that the highest sustainably controlled temperature of the reaction is maintained at a temperature of from −10 to 45° C. Even more preferably the reaction is conducted at a temperature of from 0 to 35° C. so that the highest sustainably controlled temperature is maintained at a temperature of from 0 to 35° C.

The resulting reaction mixture is usually withdrawn from the reaction vessel as an effluent, which is, for example, then immediately cooled to reduce undesirable side reactions, such as the isomerization reaction of the desired hydrogen bromide salt of the (Z)-2-aminothiazole derivative to its E-isomer. The reaction mixture is for example, cooled usually to 0° C. or less, preferably to −10° C. or less, and more preferably to −30° C. or less to effectively suppress isomerization reaction. Alternatively, the withdrawn reaction mixture may be added dropwise to an aqueous acidic solution as used in the first aspect of the present invention.

Therefore, residence time (reaction time) Rt is preferably set at a range defined by the following inequality:

$$60e^{(-0.15T)} \leq Rt \leq 180e^{(-0.1T)},$$

wherein "T" is the highest sustainably controlled temperature.

The method of cooling may be, but is not restricted to, being carried out by cooling the reaction mixture obtained indirectly using a refrigerant, or by directly pouring the reaction mixture into a solvent previously cooled such as 1-chlrobutane and the like, or by adding a cooled material such as a solvent previously cooled and/or dry ice to the effluent reaction mixture, and the like.

Alternatively, the reaction can be carried out by mixing a solution of the 2-alkylidene-4-bromoacetoacetic ester of the formula (IV) and a solution of thiourea quickly under similar reaction conditions as described above taking account of the exothermic amount of the reaction but in a single stage reaction within the above-described preferable reaction temperature and time.

The process of the present invention can preferentially produce the Z-isomer of the hydrogen bromide salt of the 2-aminothiazole derivative, which is useful as an intermediate to pharmaceuticals and can be further purified advantageously as a desired Z-isomer by the present method as described above.

EXAMPLES

The present invention will be explained in detail, but are not to be construed to limit the scope of the invention thereto.

Production Example 1 of methyl 2-propylidene-4-bromoacetoacetate

Into a solution obtained by dissolving 35.6 g (593 mmol) of acetic acid in 369 g of 1-chlorobutane, three components, including 253.5 g (1300 mmol) of methyl 4-bromoacetoacetate, 172.2 g (2964 mmol) of propionaldehyde and 12.6 g (148 mmol) of piperidine, were added separately in parallel over a period of 6 hours at −25 to −30° C. After being held at that temperature for 2 hours, the reaction mixture was poured into 378 g of a 1.4% aqueous hydrochloric acid. The mixture was heated to 5° C. and separated into an aqueous and organic layer. The organic layer was washed with 426 g of an aqueous sodium hydrogensulfite solution (40.7 g in terms of sulfurous acid gas) at 0 to 5° C., and the oil layer separated was further washed with 363 g of water to give 732 g of a solution containing 267 g (1135 mmol, 87% yield) of methyl 2-propylidene-4-bromoacetoacetate in 1-chlorobutane.

Example 1

To 18.7 g of the solution containing methyl 2-propylidene-4-bromoacetoacetate in 1-chlorobutane obtained in Production Example 1, which solution contains (6.79 g, 28.9 mmol of pure methyl 2-propylidene-4-bromoacetoacetate), 9.8 g of 1-chlorobutane and 9.8 g of acetone were added, and the mixture was cooled to −30° C. To the resulting solution, a solution obtained by dissolving 2.49 g (32.8 mmol) of thiourea in 10.3 g of N,N-dimethylformamide was poured quickly and stirred at 20° C. for 5 minutes. The mixture was poured into 9.1 g of 1-chlorobutane which had been cooled to −10° C. to give 60.2 g of a solution containing 5.08 g (17.3 mmol, 59.9% yield) of a hydrogen bromide salt of methyl (Z)-2-(2-aminothiazole-4-yl)-2-pentenoate and 2.40 g (8.2 mmol, 28.4% yield) of a hydrogen bromide salt of methyl (E)-2-(2-aminothiazole-4-yl)-2-pentenoate. (The E/Z ratio was 32/68.)

Examples 2 to 12

The results shown in Table 1 were obtained by carrying out the reaction in the same manner as Example 1 except that the reaction temperature and the reaction time were set to the values provided in Table 1.

TABLE 1

|  | Reaction temperature (° C.) | Reaction time (minute) | Z-isomer yield (%) | E/Z ratio |
|---|---|---|---|---|
| Example 2 | 20 | 10 | 57.9 | 33/67 |
| Example 3 | 20 | 15 | 57.0 | 34/66 |
| Example 4 | 20 | 20 | 56.0 | 35/65 |
| Example 5 | 25 | 5 | 58.9 | 33/67 |
| Example 6 | 25 | 7.5 | 58.3 | 33/67 |
| Example 7 | 25 | 10 | 58.2 | 34/66 |
| Example 8 | 30 | 3.5 | 57.7 | 33/67 |
| Example 9 | 30 | 5 | 57.5 | 34/66 |
| Example 10 | 30 | 7.5 | 56.5 | 35/65 |
| Example 11 | 35 | 2 | 56.4 | 34/66 |
| Example 12 | 35 | 5 | 55.5 | 36/64 |

Example 13

To 60.2 g of the solution obtained in Example 1 containing 5.08 g (17.3 mmol) of the hydrogen bromide salt of methyl (Z)-2-(2-aminothiazole-4-yl)-2-pentenoate and 2.40 g (8.2 mmol) of the hydrogen bromide salt of methyl (E)-2-(2-aminothiazole-4-yl)-2-pentenoate, 6.9 g of water was added at −15 to −10° C. and the mixture was separated into an aqueous and organic layer. To the aqueous layer was added dropwise 5.4 g (53.6 mmol) of a 36% hydrochloric acid at −10 to −5° C. over a period of 30 minutes. After being held at that temperature for 2 hours, the reaction mixture was filtered at the same temperature to give crystals. The crystals obtained were washed with two portions of 10.5 g of acetone which had been cooled to −10 to −5° C., and were dried under reduced pressure to afford 3.64 g of crystals containing an acid salt of methyl (Z)-2-(2-aminothiazole-4-yl)-2-pentenoate.

The amount of the acid salt of methyl (Z)-2-(2-aminothiazole-4-yl)-2-pentenoate contained in the crystals obtained was 3.26 g (13.1 mmol) in terms of hydrochloride. (The yield was 45.3% based on methyl 2-propylidene-4-bromoacetoacetate.) The amount of the acid salt of methyl (E)-2-(2-aminothiazole-4-yl)-2-pentenoate contained in those crystals was 0.01 g in terms of hydrochloride. The E/Z ratio of the acid salt of methyl 2-(2-aminothiazole-4-yl)-2-pentenoate was 0.4/99.6.

Examples 14 to 24

The results shown in Table 2 were obtained by carrying out the reaction in the same manner as Example 13 except for using the reaction solutions obtained in Examples 2 to 12 instead of the after reaction solution obtained in Example 1.

TABLE 2

| Example No. | Z-isomer yield (%) | E/Z ratio |
|---|---|---|
| Example 14 | 45.5 | 0.4/99.6 |
| Example 15 | 44.8 | 0.4/99.6 |
| Example 16 | 43.8 | 0.6/99.5 |
| Example 17 | 46.2 | 0.4/99.6 |
| Example 18 | 46.7 | 0.3/99.7 |
| Example 19 | 46.9 | 0.3/99.7 |
| Example 20 | 45.7 | 0.2/99.8 |
| Example 21 | 46.3 | 0.4/99.6 |
| Example 22 | 44.9 | 0.2/99.8 |
| Example 23 | 45.3 | 0.3/99.7 |
| Example 24 | 43.9 | 0.3/99.7 |

Example 25

Into a flask (capacity: 22 ml), provided with a bypass for taking out a content therethrough from the side wall of the flask, were added in parallel a solution prepared by mixing a solution of methyl 2-propylidene-4-bromoacetoacetate in 1-chlorobutane obtained in the same manner as Production Example 1 (pure methyl 2-propylidene-4-bromoacetoacetate content: 31.9% by weight) with 1.4 parts by weight (relative to pure methyl 2-propylidene-4-bromoacetoacetate) of 1-chlorobutane and 1.4 parts by weight (relative to pure methyl 2-propylidene-4-bromoacetoacetate) of acetone at a rate of 3.23 g/min and a solution prepared by dissolving thiourea in N,N-dimethylformamide (thiourea content: 19.5% by weight) at a rate of 1.00 g/min. The mixed reaction solution was held at 25° C. and the average residence time was 5 minutes. While the two solutions were stirred and mixed, the mixed reaction solution obtained was taken out through the bypass and poured into 1-chlorobutane which had been cooled to −30° C. previously to give a hydrogen bromide salt of methyl (Z)-2-(2-aminothiazole-4-yl)-2-pentenoate with a yield of 48.4%. The yield of a hydrogen bromide salt of methyl (E)-2-(2-aminothiazole-4-yl)-2-pentenoate was 23.8%. (The E/Z ratio was 33/67.)

Example 26

Into a flask (capacity: 22 ml), provided with a bypass for taking out a content therethrough from the side wall of the flask, were added in parallel a solution prepared by mixing a solution of methyl 2-propylidene-4-bromoacetoacetate in 1-chlorobutane obtained in the same manner as Production Example 1 (pure methyl 2-propylidene-4-bromoacetoacetate content: 31.9% by weight) with 1.4 parts by weight (relative to pure methyl 2-propylidene-4-bromoacetoacetate) of 1-chlorobutane and 1.4 parts by weight (relative to pure methyl 2-propylidene-4-bromoacetoacetate) of acetone at a rate of 1.61 g/min and a solution prepared by dissolving thiourea in N,N-dimethylformamide (thiourea content: 19.5% by weight) with a rate of 0.51 g/min. The mixed reaction solution was held at 25° C. and the average residence time was 10 minutes. While the two solutions were stirred and mixed, the mixed reaction solution obtained was taken out through the bypass and poured into 1-chlorobutane which had been cooled to −30° C. previously to give a hydrogen bromide salt of methyl (Z)-2-(2-aminothiazole-4-yl)-2-pentenoate with a yield of 45.9%. The yield of a hydrogen bromide salt of methyl (E)-2-(2-aminothiazole-4-yl)-2-pentenoate was 28.4%. (The E/Z ratio was 36/64.)

Example 27

Into a pipe (capacity: 1116 ml) connected to a VIBRO MIXER® (capacity: 192 ml) manufactured by Reika Kogyo Co. were added dropwise in parallel a solution prepared by mixing a solution of methyl 2-propylidene-4-bromoacetoacetate in 1-chlorobutane obtained in the same manner as Production Example 1 (pure methyl 2-propylidene-4-bromoacetoacetate content: 32.3% by weight) with 1.56 parts by weight (relative to pure methyl 2-propylidene-4-bromoacetoacetate) of 1-chlorobutane and 1.56 parts by weight (relative to pure methyl 2-propylidene-4-bromoacetoacetate) of acetone at a rate of 97.8 g/min and a solution prepared by dissolving thiourea in N,N-dimethylformamide (thiourea content: 19.8% b y weight) at a rate of 29.6 g/min. The mixed reaction solution was held at 25° C. and the average residence time was 10 minutes. While the two solutions were stirred and mixed, the mixed reaction solution obtained was taken out through the outlet of the pipe and poured into 1-chlorobutane which had been cooled to −18 to −15° C. previously to give a hydrogen bromide salt of methyl (Z)-2-(2-aminothiazole-4-yl)-2-pentenoate with a yield of 58.7%. The yield of a hydrogen bromide salt of methyl (E)-2-(2-aminothiazole-4-yl)-2-pentenoate was 29.5%. (The E/Z ratio was 33/67.)

Example 28

Into a tubular reactor having a static mixer (capacity: 3.9 ml, number of element to cause turbulance to the flow: 24) to which is connected a pipe (capacity: 4164 ml) were charged in parallel a solution prepared by mixing a solution of methyl 2-propylidene-4-bromoacetoacetate in 1-chlorobutane obtained in the same manner as Production Example 1 (pure methyl 2-propylidene-4-bromoacetoacetate content: 33.4% by weight) with 1.4 parts by weight (relative to pure methyl 2-propylidene-4-bromoacetoacetate) of 1-chlorobutane and 1.4 parts by weight (relative to pure methyl 2-propylidene-4-bromoacetoacetate) of acetone at a rate of 297.5 g/min and a solution prepared by dissolving thiourea in N,N-dimethylformamide (thiourea content: 19.5% by weight) at a rate of 87.9 g/min, while the reaction mixture was maintained at 25° C. and the average residence time was maintained 10 minutes. The mixed reaction solution obtained was taken out through the outlet of the pipe and poured into 1-chlorobutane which had been cooled to −20 to −15° C. previously to give a hydrogen bromide salt of methyl (Z)-2-(2-aminothiazole-4-yl)-2-pentenoate in a yield of 63.5%. The yield of a hydrogen bromide salt of methyl (E)-2-(2-aminothiazole-4-yl)-2-pentenoate was 25.0%. (The E/Z ratio was 28/72.)

Example 29

To 66.0 g of the solution containing 4.39 g (15.0 mmol) of the hydrogen bromide salt of methyl (Z)-2-(2-aminothiazole-4-yl)-2-pentenoate and 2.16 g (7.4 mmol) of the hydrogen bromide salt of methyl (E)-2-(2-aminothiazole-4-yl)-2-pentenoate obtained in Example 13 was added 5.1 g of water at −15 to −10° C., and the resulting mixture was separated into an aqueous and organic layer. To the aqueous layer was added 5.6 g (55.7 mmol) of a 36% hydrochloric acid at −10 to −5° C. over a period of 30 minutes. After being held at that temperature for 2 hours, the reaction mixture was filtered to give crystals. The crystals obtained were washed with two portions of 10.9 g of acetone which had been cooled to −10 to −5° C., and were dried in vacuo to give 2.69 g of crystals containing an acid salt of methyl (Z)-2-(2-aminothiazole-4-yl)-2-pentenoate.

The amount of the acid salt of methyl (Z)-2-(2-aminothiazole-4-yl)-2-pentenoate contained in the crystals obtained was 2.42 g (9.74 mmol) in terms of hydrochloride. (The yield was 31.5% based on methyl 2-propylidene-4-bromoacetoacetate.) The amount of the acid salt of methyl (E)-2-(2-aminothiazole-4-yl)-2-pentenoate contained in those crystals was 0.02 g in terms of hydrochloride. The E/Z ratio of the acid salt of methyl 2-(2-aminothiazole-4-yl)-2-pentenoate was 0.7/99.3.

Example 30

To 64.1 g of the solution containing 4.03 g (13.8 mmol) of the hydrogen bromide salt of methyl (Z)-2-(2-aminothiazole-4-yl)-2-pentenoate and 3.32 g (7.9 mmol) of the hydrogen bromide salt of methyl (E)-2-(2-aminothiazole-4-yl)-2-pentenoate obtained in Example 14 was added 4.9 g of water at −15 to −10° C., and the resulting mixture was separated into an aqueous and organic layer. To the aqueous layer was added 5.5 g (53.9 mmol) of a 36% hydrochloric acid at −10 to −5° C. over a period of 30 minutes. After being held at that temperature for 2 hours, the reaction mixture was filtered to give crystals. The crystals obtained were washed with two portions of 10.6 g of acetone which had been cooled to −10 to −5° C., and were dried in vacuous to give 2.57 g of crystals containing an acid salt of methyl (Z)-2-(2-aminothiazole-4-yl)-2-pentenoate.

The amount of the acid salt of methyl (Z)-2-(2-aminothiazole-4-yl)-2-pentenoate contained in the crystals obtained was 2.24 g (8.99 mmol) in terms of hydrochloride. (The yield was 30.0% based on methyl 2-propylidene-4-bromoacetoacetate.) The amount of the acid salt of methyl (E)-2-(2-aminothiazole-4-yl)-2-pentenoate contained in those crystals was 0.02 g in terms of hydrochloride. The E/Z ratio of the acid salt of methyl 2-(2-aminothiazole-4-yl)-2-pentenoate was 0.7/99.3.

Example 31

To 108.15 kg of the solution containing 8.68 kg (29.6 mol) of the hydrogen bromide salt of methyl (Z)-2-(2-aminothiazole-4-yl)-2-pentenoate and 4.36 kg (14.9 mol) of the hydrogen bromide salt of methyl (E)-2-(2-aminothiazole-4-yl)-2-pentenoate obtained in Example 15 was added 8.30 kg of water at −18 to −16° C., and the resulting mixture was separated into an aqueous and organic layer. To the aqueous layer was added 8.88 kg (85.2 mol) of a 36% hydrochloric acid at −13 to −7° C. over a period of 2 hours. After being held at that temperature for 2 hours, the reaction mixture was filtered to give crystals. The crystals obtained were washed with four portions of 9.1 kg of acetone which had been cooled to −10 to −5° C. to give 7.00 kg of crystals containing an acid salt of methyl (Z)-2-(2-aminothiazole-4-yl)-2-pentenoate.

The amount of the acid salt of methyl (Z)-2-(2-aminothiazole-4-yl)-2-pentenoate contained in the crystals obtained was 5.94 kg (23.9 mol) in terms of hydrochloride. (The yield was 47.3% based on methyl 2-propylidene-4-bromoacetoacetate.) The amount of the acid salt of methyl (E)-2-(2-aminothiazole-4-yl)-2-pentenoate contained in those crystals was 0.02 kg in terms of hydrochloride. The E/Z ratio of the acid salt of methyl 2-(2-aminothiazole-4-yl)-2-pentenoate was 0.4/99.6.

Example 32

To 61.57 g of a solution containing 5.54 g (18.91 mmol) of the hydrogen bromide salt of methyl (Z)-2-(2-aminothiazole-4-yl)-2-pentenoate and 2.18 g (7.44 mmol) of the hydrogen bromide salt of methyl (E)-2-(2-aminothiazole-4-yl)-2-pentenoate obtained in Example 16 was added 4.90 g of water at −20 to −15° C., and the resulting mixture was separated into an aqueous and organic layer. To the aqueous layer was added 3.53 g of acetone and then 5.58 g (53.60 mmol) of a 36% hydrochloric acid at −10 to −5° C. over a period of 0.5 hour. After being held at that temperature for 2 hours, the reaction mixture was filtered to give crystals. The crystals obtained were washed with two portions of 10.52 g of acetone which had been cooled to −10 to −5° C. to give 4.22 g of crystals containing an acid salt of methyl (Z)-2-(2-aminothiazole-4-yl)-2-pentenoate.

The amount of the acid salt of methyl (Z)-2-(2-aminothiazole-4-yl)-2-pentenoate contained in the crystals obtained was 3.83 g (15.41 mmol) in terms of hydrochloride. (The yield was 51.7% based on methyl 2-propylidene-4-bromoacetoacetate.) The amount of the acid salt of methyl (E)-2-(2-aminothiazole-4-yl)-2-pentenoate contained in those crystals was 0.015 g in terms of hydrochloride. The E/Z ratio of the acid salt of methyl 2-(2-aminothiazole-4-yl)-2-pentenoate was 0.4/99.6.

Production Example 2 of methyl 2-propylidene-4-bromoacetoacetate

Into a solution obtained by dissolving 8.14 g (136 mmol) of acetic acid in 81.6 g of methyl isobutyl ketone, three solutions of 58.5 g (300 mmol) of methyl 4-bromoacetoacetate, 39.4 g (678 mmol) of propionaldehyde and 2.89 g (33.9 mmol) of piperidine in 3.50 g of methyl isobutyl ketone were added dropwise in parallel (added simultaneously) over a period of 6 hours at −25 to −30° C. To the mixture which had been held at that temperature for three hours was added 170 g of methyl isobutyl ketone, and the resultant reaction mixture was poured into 86.5 g of a 1.4% aqueous hydrochloric acid. The mixture was heated to 5° C. and separated into an aqueous and organic layer. The organic layer was washed with 45.1 g of aqueous sodium hydrogensulfite solution (4.5 g in terms of sulfurous acid) at 0 to 5° C. The resultant oil layer was further washed with 86.5 g of water to give 342 g of a solution containing 61.6 g (262 mmol, 88% yield) of methyl 2-propylidene-4-bromoacetoacetate in methyl isobutyl ketone. This solution was used directly in the next reaction without concentrating or the like.

Example 33

To 39.6 g of a solution containing methyl 2-propylidene-4-bromoacetoacetate in methyl isobutyl ketone obtained in Production Example 2 (7.0 g, 30 mmol in terms of pure methyl 2-propylidene-4-bromoacetoacetate), which had been cooled to −30° C. previously, a solution obtained by dissolving 2.5 g (33 mmol) of thiourea in 10.4 g of N,N-dimethylformamide was poured quickly. The mixture was elevated in temperature and thereafter stirred at 20° C. for 10 minutes. In 52.5 g of the resultant reaction mixture, 7.3 g of methyl 2-(2-aminothiazole-4-yl)-2-pentenoate hydrobromide (E/Z ratio=33/67, 56% Z-isomer yield) was contained.

To 40.9 g of methyl ethyl ketone which had been cooled to −10° C., the foregoing reaction mixture was poured and cooled. To the resulting mixture was added 11.2 g (49 mmol) of 16% aqueous hydrochloric acid at −10 to −5° C. over a period of 30 minutes. After being held at that temperature for 2 hours, the reaction mixture was filtered at the same temperature to give crystals. The resulting crystals were washed with a portion of 10.5 g of methyl isobutyl ketone which had been cooled to −10 to −5° C. and with two portions of 10.5 g of acetone which had been cooled to −10 to −5° C., and were dried in vacuo to afford 3.57 g of crystals containing an acid salt of methyl (Z)-2-(2-aminothiazole-4-yl)-2-pentenoate.

The amount of the acid salt of methyl (Z)-2-(2-aminothiazole-4-yl)-2-pentenoate contained in the crystals obtained was 3.20 g (12.9 mmol) in terms of hydrochloride. (The yield was 43% based on methyl 2-propylidene-4-bromoacetoacetate). The amount of the acid salt of methyl (E)-2-(2-aminothiazole-4-yl)-2-pentenoate contained in those crystals was 0.02 g in terms of hydrochloride. The E/Z ratio of the acid salt of methyl 2-(2-aminothiazole-4-yl)-2-pentenoate was 0.6/99.4.

Example 34

To 59.4 g of a solution containing methyl 2-propylidene-4-bromoacetoacetate obtained in the same manner as Production Example 2 (10.0 g, 43 mmol in terms of pure methyl 2-propylidene-4-bromoacetoacetate) in methyl isobutyl ketone, which had been cooled to −30° C. previously, a solution obtained by dissolving 3.56 g (47 mmol) of thiourea in 14.7 g of N,N-dimethylformamide was poured quickly. The mixture was elevated in temperature and thereafter stirred at 20° C. for 10 minutes. In 77.7 g of the resultant reaction mixture, 10.8 g of methyl 2-(2-aminothiazole-4-yl)-2-pentenoate hydrobromide (E/Z ratio=33/67, 59% Z-isomer yield) was contained.

To 38.8 g (77.6 mmol) of 7.3% aqueous hydrochloric acid, the foregoing reaction mixture was poured at −8 to 0° C. over a period of 2 minutes. After being held at −10 to −5° C. for 2 hours, the reaction mixture was filtered at that temperature to give crystals. The resulting crystals were washed with a portion of 17 g of methyl isobutyl ketone cooled to −10 to −5° C. and with two portions of 15 g and 10 g of acetone cooled to −10 to −5° C., and were dried in vacuo to afford 5.58 g of crystals containing the acid salt of methyl (Z)-2-(2-aminothiazole-4-yl)-2-pentenoate.

The composition of the resultant crystals was 4.16 g of the Z-isomer in terms of free (Z)-2-(2-aminothiazole-4-yl)-2-pentenoate (content in crystals: 74.6%, 19.6 mmol; yield based on 2-propylidene-4-bromoacetoacetate: 46%) and 0.02 g of the E-isomer in terms of free (E)-2-(2-aminothiazole-4-yl)-2-pentenoate (content in crystals: 0.44%, 0.11 mmol). (The E/Z ratio was 0.6/99.4.)

As acidic components 0.59 g of hydrogen chloride (content in crystals: 10.5%, 16.2 mmol) and 0.47 g of hydrogen bromide (content in crystals: 8.4%, 5.9 mmol) were contained in the crystals. The amount of moisture contained in the crystals was 0.35 g (content in crystals: 6.2%, 19.5 mmol).

The total content of the foregoing components in the crystals were 100%.

Example 35

To 59.4 g of a solution containing methyl 2-propylidene-4-bromoacetoacetate obtained in the same manner as Production Example 2 (10.0 g, 43 mmol in terms of pure methyl 2-propylidene-4-bromoacetoacetate) in methyl isobutyl ketone, which had been cooled to −30° C. previously, a solution obtained by dissolving 3.56 g (47 mmol) of thiourea in 14.7 g of N,N-dimethylformamide was poured quickly. The mixture was elevated in temperature and thereafter stirred at 0° C. for 5 minutes. To 38.8 g (77.6 mmol) of 7.3% aqueous hydrochloric acid, 77.7 g of the reaction mixture obtained above was poured at −10 to −3° C. over a period of 2 minutes. After being held at 0° C. for 1.5 hours, the reaction mixture was cooled to −10° C. over a period of 0.5 hour and held at −10° C. for 0.5 hour. The resultant reaction mixture was filtered at that temperature to give crystals. The resulting crystals were washed with a portion of 15 g of methyl isobutyl ketone cooled to −10° C. and with two portions of 15 g of acetone cooled to −10° C., and were dried in vacuo to afford 5.50 g of crystals containing the acid salt of methyl (Z)-2-(2-aminothiazole-4-yl)-2-pentenoate.

In the crystals, there was 4.92 g (19.8 mmol) in terms of hydrochloride of the acid salt of methyl (Z)-2-(2-aminothiazole-4-yl)-2-pentenoate. (The yield was 46% based on methyl 2-propylidene-4-bromoacetoacetate.) The content of the acid salt of (E)-2-(2-aminothiazole-4-yl)-2-pentenoate in the crystals was 0.01 g in terms of hydrochloride. The E/Z ratio of the acid salt of 2-(2-aminothiazole-4-yl)-2-pentenoate was 0.2/99.8.

Example 36

To 41.2 g of a solution containing methyl 2-propylidene-4-bromoacetoacetate obtained in the same manner as Production Example 2 (7.0 g, 30 mmol in terms of pure methyl 2-propylidene-4-bromoacetoacetate) in methyl isobutyl ketone, which had been cooled to −30° C. previously, a solution obtained by dissolving 2.49 g (33 mmol) of thiourea in 10.3 g of N,N-dimethylformamide was poured quickly. The mixture was elevated in temperature and thereafter stirred at 20° C. for 10 minutes. To 54.0 g of the reaction mixture obtained, 12.5 g (54 mmol) of 15.8% aqueous hydrochloric acid was poured at −10 to −5° C. over a period of 30 minutes. After being held at that temperature for 2 hours, the resultant reaction mixture was filtered at the same temperature to give crystals. The resulting crystals were washed with two portions of 10.5 g of acetone cooled to −10° C., and were dried in vacuo to afford 3.99 g of crystals containing the acid salt of methyl (Z)-2-(2-aminothiazole-4-yl)-2-pentenoate.

In the crystals, there was 3.52 g (14.2 mmol) in terms of hydrochloride of the acid salt of methyl (Z)-2-(2- aminothiazole-4-yl)-2-pentenoate. (The yield was 48% based on methyl 2-propylidene-4-bromoacetoacetate.) The content of the acid salt of (E)-2-(2-aminothiazole-4-yl)-2-pentenoate in the crystals was 0.02 g in terms of hydrochloride. The E/Z ratio of the acid salt of 2-(2-aminothiazole-4-yl)-2-pentenoate was 0.7/99.3.

Production Example 3 of methyl 2-propylidene-4-bromoacetoacetate

Into a solution obtained by dissolving 27.5 g (0.46 mmol) of acetic acid in 272 g of 1-chlorobutane, 195 g (1.00 mol) of methyl 4-bromoacetoacetate, 133 g (2.29 mol) of propionaldehyde and 9.73 g (0.11 mmol) of piperidine, were added dropwise separately in parallel over a period of 6 hours at −25 to −30° C. After being held at that temperature for 2 hours, the reaction mixture was poured into 292 g of a 1.4% aqueous hydrochloric acid. The mixture was heated to 5° C. and separated into an aqueous and organic layer. The organic layer was washed with 358 g of an aqueous sodium hydrogensulfite solution (35.8 g in terms of sulfurous acid) at 0 to 5° C. and separated into two layers. The resultant oil layer was further washed with 292 g of water to give 551 g of a solution containing 207 g (0.88 mol, 88% yield) of methyl 2-propylidene-4-bromoacetoacetate in 1-chlorobutane. This solution was used directly in the next reaction without being subjected to concentration or the like.

Example 357

To 18.6 g of a solution containing methyl 2-propylidene-4-bromoacetoacetate in 1-chlorobutane obtained in Production Example 3 (7.0 g, 30 mmol in terms of pure methyl 2-propylidene-4-bromoacetoacetate), 9.8 g of 1-chlorobutane and 9.8 g of acetone were added, and the mixture was cooled to −30° C. To the resulting mixture, a solution obtained by dissolving 2.5 g (33 mmol) of thiourea in 10.3 g of N,N-dimethylformamide was poured quickly. The mixture was elevated in temperature and thereafter stirred at 20° C. for 10 minutes. In the resultant reaction mixture, 7.8 g of methyl 2-(2-aminothiazole-4-yl)-2-pentenoate hydrobromide (E/Z ratio=30/70, 63% Z-isomer yield) was contained.

To 9.1 g of 1-chlorobutane which had been cooled to −10° C., the foregoing reaction mixture was poured and cooled. To the resulting mixture was added 6.9 g of water and the mixture was separated into an aqueous and organic layer at −3° C. To the thus obtained aqueous solution containing methyl 2-(2-aminothiazole-4-yl)-2-pentenoate hydrobromide was added 5.4 g (54 mmol) of a 36% aqueous hydrochloric acid at −10 to −5° C. over a period of 30 minutes. After being held at that temperature for 2 hours, the reaction mixture was filtered at the same temperature to give crystals. The resulting crystals were washed with two portions of 10.5 g of acetone which had been cooled to −10 to −5° C., and were dried in vacuous to afford 3.83 g of crystals containing an acid salt of methyl (Z)-2-(2-aminothiazole-4-yl)-2-pentenoate.

The amount of the acid salt of methyl (Z)-2-(2-aminothiazole-4-yl)-2-pentenoate contained in the crystals obtained was 3.36 g (13.5 mmol) in terms of hydrochloride. (The yield was 45% based on methyl 2-propylidene-4-bromoacetoacetate.) The amount of the acid salt of methyl (E)-2-(2-aminothiazole-4-yl)-2-pentenoate contained in those crystals was 0.03 g in terms of hydrochloride. The E/Z ratio of the acid salt of methyl 2-(2-aminothiazole-4-yl)-2-pentenoate was 0.9/99.1.

Example 38

In the same manner as Example 37 except for adding the aqueous solution containing methyl 2-(2-aminothiazole-4-yl)-2-pentenoate hydrobromide to 5.4 g of a 36% aqueous hydrochloric acid (54 mmol) at −10 to −5° C., 3.87 g of crystals containing the acid salt of methyl (Z)-2-(2-aminothiazole-4-yl)-2-pentenoate was obtained.

The amount of the acid salt of methyl (Z)-2-(2-aminothiazole-4-yl)-2-pentenoate contained in the crystals obtained was 3.44 g (13.8 mmol) in terms of hydrochloride. (The yield was 46% based on methyl 2-propylidene-4-bromoacetoacetate.) The amount of the acid salt of methyl (E)-2-(2-aminothiazole-4-yl)-2-pentenoate contained in those crystals was 0.02 g in terms of hydrochloride. The E/Z ratio of the acid salt of methyl 2-(2-aminothiazole-4-yl)-2-pentenoate was 0.6/99.4.

Example 39

In the same manner as Example 37 except that about 3 mg of crystals of methyl (Z)-2-(2-aminothiazole-4-yl)-2-pentenoate hydrochloride was added, and then 1.8 g of a 36% aqueous hydrochloric acid (18 mmol) was added to the aqueous solution containing methyl 2-(2-aminothiazole-4-yl)-2-pentenoate hydrobromide at −10 to −5° C., and stirring at that temperature for 30 minutes to form crystals, and thereafter 3.6 g of a 36% aqueous hydrochloric acid (36 mmol) was added at the same temperature over a period of 1 hour, 3.82 g of crystals containing the acid salt of methyl (Z)-2-(2-aminothiazole-4-yl)-2-pentenoate was obtained.

The amount of the acid salt of methyl (Z)-2-(2-aminothiazole-4-yl)-2-pentenoate contained in the crystals obtained was 3.37 g (13.5 mmol) in terms of hydrochloride. (The yield was 45% based on methyl 2-propylidene-4-bromoacetoacetate.) The amount of the acid salt of methyl (E)-2-(2-aminothiazole-4-yl)-2-pentenoate contained in those crystals was 0.02 g in terms of hydrochloride. The E/Z ratio of the acid salt of methyl 2-(2-aminothiazole-4-yl)-2-pentenoate was 0.5/99.5.

Example 40

To 18.0 g of a solution containing methyl 2-propylidene-4-bromoacetoacetate in 1-chlorobutane obtained in the same manner as Production Example 3 (7.0 g, 30 mmol in terms of pure methyl 2-propylidene-4-bromoacetoacetate), which had been cooled to −30° C., a solution obtained by dissolving 2.5 g (33 mmol) of thiourea in 10.3 g of N,N-dimethylformamide was poured quickly. The mixture was elevated in temperature and thereafter stirred at 20° C. for 10 minutes. The resultant reaction mixture was added to 27.2 g of a 7.3% aqueous hydrochloric acid (54 mmol) at −6 to −5° C. over a period of 5 minutes and held at −10 to −5° C. for 2 hours. The reaction mixture was filtered at that temperature to give crystals. The resulting crystals were washed with two portions of 10.5 g of acetone which had been cooled to −10 to −5° C., and were dried in vacuo to afford 4.06 g of crystals containing an acid salt of methyl (Z)-2-(2-aminothiazole-4-yl)-2-pentenoate.

The amount of the acid salt of methyl (Z)-2-(2-aminothiazole-4-yl)-2-pentenoate contained in the crystals obtained was 3.54 g (14.2 mmol) in terms of hydrochloride. (The yield was 48% based on methyl 2-propylidene-4-bromoacetoacetate.) The amount of the acid salt of methyl (E)-2-(2-aminothiazole-4-yl)-2-pentenoate contained in those crystals was 0.04 g in terms of hydrochloride. The E/Z ratio of the acid salt of methyl 2-(2-aminothiazole-4-yl)-2-pentenoate was 1.0/99.0.

Production Example 4 of methyl 2-propylidene-4-bromoacetoacetate

In 105.76 g of methyl isobutyl ketone, 75.01 g of methyl 4-chloroacetoacetate, 43.41 g of propionaldehyde and 2.99 g of acetic acid were dissolved. After cooling the mixture to −30° C., a mixed solution of 2.54 g of piperidine and 3.44 g of methyl isobutyl ketone was added at −27±2° C. over a period of 30 minutes. After holding the reaction mixture at that temperature for 2 hours, 295.5 g of a 0.35% aqueous hydrochloric acid and 10.6 g of methyl isobutyl ketone were added to the mixture. The mixture was heated to 3° C. and separated into an aqueous and organic layer. The organic layer was washed at 0 to 5° C. with 295.5 g of a 1% aqueous sodium hydrogencarbonate solution and 295.5 g of water in this order to give 192.03 g of a solution of methyl 2-propylidene-4-chloroacetoacetate.

To 191.68 g of this solution was added 203.49 g of N,N-dimethylformamide, and the mixture was cooled to 10° C. To this mixture was added 122.80 g of sodium bromide, and the mixture was heated to 22° C. and stirred vigorously for 3 hours. The resultant reaction solution was cooled to 5° C., washed with 356 g of water, and then separated to give 202.27 g of a solution of methyl 2-propylidene-4-bromoacetoacetate in methyl isobutyl ketone (the solution containing 80.83 g of methyl 2-propylidene-4-bromoacetoacetate).

Example 41

To 8.11 g of the methyl 2-propylidene-4-bromoacetoacetate solution in methyl isobutyl ketone obtained in Production Example 4 (3.24 g in terms of pure methyl 2-propylidene-4-bromoacetoacetate), a solution obtained by dissolving 1.50 g of thiourea in 6.19 g of N,N-dimethylformamide was added quickly and stirred at 20° C. for 5 minutes. The foregoing reaction mixture was poured into a mixture of 29.15 g of a 2.7% aqueous sodium hydroxide solution and 7.95 g of methyl isobutyl ketone, the mixture having been cooled to 0 to 5° C. previously, and 4.65 g of methyl isobutyl ketone was further added. The resultant mixture was then separated to give 22.5 g of an organic layer and 38.4 g of an aqueous layer. The high-performance liquid chromatography analysis indicated that the organic layer contained 1.52 g of methyl (Z)-2-(2-aminothiazole-4-yl)-2-pentenoate and 0.68 g of methyl (E)-2-(2-aminothiazole-4-yl)-2-pentenoate and the aqueous layer contained 0.09 g of methyl (Z)-2-(2-aminothiazole-4-yl)-2-pentenoate and 0.09 g of methyl (E)-2-(2-aminothiazole-4-yl)-2-pentenoate. The analysis also indicated that the total yield of methyl (Z)-2-(2-aminothiazole-4-yl)-2-pentenoate in the organic and aqueous layers was 56.4% and the E/Z ratio was 32.4/67.6.

Examples 42 to 52

The results shown in Table 3 were obtained by carrying out the reaction and the post-treatment in the same manner as Example 41 except that the reaction temperature and the reaction time were set to the values provided in Table 3.

TABLE 3

| | Reaction temperature (° C.) | Reaction time (minute) | Z-isomer yield (%) | E/Z ratio |
|---|---|---|---|---|
| Example 42 | 30 | 1 | 57.6 | 34/66 |
| Example 43 | 30 | 3 | 57.4 | 36/64 |
| Example 44 | 30 | 5 | 55.7 | 38/62 |
| Example 45 | 25 | 2 | 54.2 | 32/68 |
| Example 46 | 25 | 5 | 57.8 | 35/65 |
| Example 47 | 25 | 10 | 56.6 | 38/62 |
| Example 48 | 20 | 10 | 57.9 | 34/65 |
| Example 49 | 15 | 20 | 55.7 | 34/66 |
| Example 50 | 10 | 30 | 57.7 | 33/67 |

TABLE 3-continued

| | Reaction temperature (° C.) | Reaction time (minute) | Z-isomer yield (%) | E/Z ratio |
|---|---|---|---|---|
| Example 51 | 5 | 50 | 57.4 | 33/67 |
| Example 52 | 0 | 120 | 56.7 | 33/67 |

Comparative Example 1 to 4

The results shown in Table 4 were obtained by carrying out the reaction and the post-treatment in the same manner as Example 41 except that the reaction temperature and the reaction time were set to the values provided in Table 4.

TABLE 4

| | Reaction temperature (° C.) | Reaction time (minute) | Z-isomer yield (%) | E/Z ratio |
|---|---|---|---|---|
| Comparative Example 1 | 0 | 20 | 38.7 | 28/72 |
| Comparative Example 2 | 5 | 10 | 41.3 | 27/73 |
| Comparative Example 3 | 20 | 60 | 37.6 | 43/57 |
| Comparative Example 4 | 30 | 40 | 36.2 | 62/38 |

Production Example 5 of methyl 2-propylidene-4-bromoacetoacetate

In 34 g of dichloromethane, 5.0 g of methyl 4-bromoacetoacetate (purity: 95.6% ), 2.23 g of propionaldehyde and 0.15 g of acetic acid were dissolved. After cooling the mixture to −30° C., a mixed solution of 0.26 g of piperidine and 1.18 g of dichloromethane was added at −27±2° C. over a period of 30 minutes. After holding the reaction mixture at that temperature for 3.5 hours, 15 g of a 0.7% aqueous hydrochloric acid was added to the mixture. The resulting mixture was heated to 3° C. and separated into an aqueous and organic layer. The organic layer was washed at 0 to 5° C. with 15 g of a 1% aqueous sodium hydrogen-carbonate solution and 15 g of water in this order and concentrated in vacuous at a temperature not higher than 15° C. to give 8.57 g of a concentrated solution of methyl 2-propylidene-4-bromoacetoacetate (the solution containing 5.31 g of methyl 2-propylidene-4-bromoacetoacetate).

Example 53

To 8.57 g of the methyl 2-propylidene-4-bromoacetoacetate solution in dichloromethane obtained in Production Example 5 (5.31 g in terms of pure methyl 2-propylidene-4-bromoacetoacetate), 14.16 g of N,N-dimethylformamide and 7.97 g of dichloromethane were added. To this mixture, a solution obtained by dissolving 1.87 g of thiourea in 10.49 g of N,N-dimethylformamide was added at one time and stirred at 15° C. for 10 minutes. The foregoing reaction mixture was poured into a mixture of 36.4 g of a 2.7% aqueous sodium hydroxide solution and 13.3 g of dichloromethane, the mixture having been cooled to 0 to 5° C. previously, and then the resultant mixture was separated into an aqueous and organic layer. The resulting organic layer was washed with two portions of 47.7 g of a 3% saline solution at 0 to 5° C. and the aqueous layer was extracted with 13.3 g of dichloromethane. The organic layers obtained were combined and concentrated in vacuo at a temperature not higher than 15° C. to give 6.85 g of a concentrated solution of methyl 2-(2-aminothiazole-4-yl)-2-pentenoate. In this solution, 2.33 g of methyl (Z)-2-(2-aminothiazole-4-yl)-2-pentenoate (51.7% yield) and 1.10 g of methyl (E)-2-(2-aminothiazole-4-yl)-2-pentenoate were contained. The E/Z ratio was 28/72.

What is claimed is:

1. A continuous process for preferentially producing a Z-isomer of a hydrogen bromide salt of a 2-aminothiazole derivative of the formula (IV):

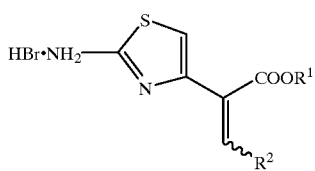

wherein $R^1$ and $R^2$ independently represent a lower alkyl group having 1 to 5 carbon atoms, and the wavy line means that this compound is a mixture of the E- and Z-isomers, which process comprises:

continuously feeding thiourea and a 2-alkylidene-4-bromoacetoacetic ester of the formula (V):

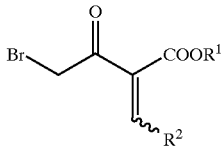

wherein $R^1$ and $R^2$ have the same meanings as defined above, and the wavy line means that this compound is a mixture of the E- and Z-isomers, into a reaction vessel having at least one agitator, reacting the thiourea and the compound of the formula (V) together for a sufficient residence time Rt in the reaction vessel to produce a conversion of the compound of the formula (V) into said compound of the formula (IV), and withdrawing a reaction mixture from the reaction vessel containing the compound of the formula (IV) as an effluent.

2. The process according to claim 1, wherein the reaction of the thiourea with the halogenated compound of the formula (V) takes place at a reaction temperature of −10 to +45° C.

3. The process according to claim 2, wherein the residence time Rt is defined by the following inequality:

$$60e^{(-0.15T)} \leq Rt \leq 180e^{(-0.1T)},$$

wherein "T" means a reaction temperature of the reaction in the reaction vessel.

4. The process according to claim 1, wherein the agitator is a static mixer or an agitator having a helical vane fixed to a shaft which is set in a tubular casing and the shaft is connected to a vibration source.

5. A process for preferentially producing a Z-isomer of a hydrogen bromide salt of a 2-aminothiazole derivative of the formula (IV):

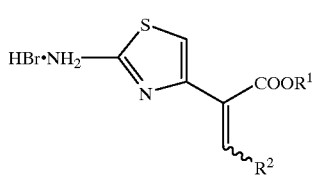

wherein $R^1$ and $R^2$ independently represent a lower alkyl group having 1 to 5 carbon atoms and the wavy line means that this compound is a mixture of the E- and Z-isomers, which process comprises:

reacting thiourea with a 2-alkylidene-4-bromoacetoacetic ester of the formula (V):

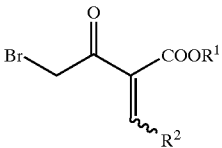

wherein $R^1$ and $R^2$ have the same meaning as defined above and the wavy line means that this compound is a mixture of the E- and Z-isomers, in a reaction mixture at a reaction temperature of −10 to +45° C. for a reaction time Rt defined by the following inequality:

$$60e^{(-0.15T)} \leq Rt \leq 180e^{(-0.1T)},$$

wherein "T" means a reaction temperature of the reaction.

* * * * *

UNITED STATES PATENT AND TRADEMARK OFFICE
CERTIFICATE OF CORRECTION

PATENT NO.     : 6,403,572 B1
DATED          : June 11, 2002
INVENTOR(S)    : Isao Kurimoto et al.

It is certified that error appears in the above-identified patent and that said Letters Patent is hereby corrected as shown below:

<u>Title page,</u>
Item [30], Foreign Application Priority Data, please correct the first priority date from "Feb. 4, 1998" to -- Feb. 4, 1999 --.

Signed and Sealed this

Thirty-first Day of December, 2002

JAMES E. ROGAN
*Director of the United States Patent and Trademark Office*